United States Patent [19]

Casimir-Schenkel et al.

[11] Patent Number: 5,407,827
[45] Date of Patent: Apr. 18, 1995

[54] PULP BLEACHING WITH THERMO STABLE XYLANASE OF THERMOMONOSPORAFUSCA

[75] Inventors: Jutta Casimir-Schenkel, Zurich, Switzerland; Susan Davis, Leeds, Great Britain; Armin Fiechter, Rudolfstetten, Switzerland; Beat Gysin, Harrogate, Great Britain; Elizabeth Murray, Leeds, Great Britain; Jean-Jacques Perrolaz, Bradford, Great Britain; Wolfgang Zimmermann, Watt, Switzerland

[73] Assignee: Sandoz Ltd., Basel, Switzerland

[21] Appl. No.: 747,768

[22] Filed: Aug. 20, 1991

[30] Foreign Application Priority Data

Aug. 22, 1990 [GB] United Kingdom ............. 9018426

[51] Int. Cl.$^6$ .................. C07G 17/00; C08B 1/00; C12N 9/24; D21C 9/00
[52] U.S. Cl. .................. 435/278; 435/267; 435/274; 435/200; 435/165; 162/9
[58] Field of Search ............. 435/278, 165, 170, 200, 435/822, 262, 267, 274; 162/9

[56] References Cited

FOREIGN PATENT DOCUMENTS 0351655 1/1990 European Pat. Off. ....... D21C 9/00

OTHER PUBLICATIONS

Chemical Abstracts CA112(22):200967p issued 1992. "Treatment of mechanical pulps with enzymes for improved drainability" EP351655 Karsila et al.
Chemical Abstracts CA 116(13):123933c issued 1991. "Thermostable hemicellulases from *Bacillus steanothermophilus* for pulp bleaching". WO9118976 Zamost et al.
Chemical Abstracts CA 115(12):116660n issued 1990. "Bleaching of pulp using xylanase". WO90FI195 Kruss et al.
McCarthy et al. "Studies of the extracellular xylanase activity of some thermophilicactinonycetes". *Applied Microbiology and Biotechnology*. vol. 21 (1985) pp. 238–244.
Chemical Abstracts CA114(24):230934j issued 1992, "Treatment of ligno cellulosic pulp with xylanase and chlorination bleaching." WO9102839 Pedensen et al.

*Primary Examiner*—Michael G. Wityshyn
*Assistant Examiner*—T. J. Reardon
*Attorney, Agent, or Firm*—Robert S. Honor; Richard E. Vila; Andrew N. Parfomak

[57] ABSTRACT

Bleaching pulp with an enzyme system, containing thermostatic xylanose activity, obtained from a strain of *Thermomonospora fusca* and more specifically from a new strain with the designation KW3 and deposition number DSM 6013.

12 Claims, No Drawings

PULP BLEACHING WITH THERMO STABLE XYLANASE OF THERMOMONOSPORAFUSCA

This invention relates to the use of thermostable enzyme systems obtained from *Thermomonospora fusca* strains and to a new bacterial strain, *Thermomonospora fusca* with the designation KW3, and its thermostable enzymes which are active over a wide pH range and at higher temperatures to modify wood pulp properties especially to reduce the lignin content.

Wood is a complex material which is composed of cellulose, hemicellulose and lignin along with other minor components. Lignin is associated and probably also covalently bound to cellulose and hemicellulose (polymers of various hexoses and penroses e.g. xylans).

In the paper-making process, lignin is generally removed from the wood pulp since it lends a brownish color, reduces strength and imparts other undesirable characteristics to the finished product. Removal of lignin can be achieved in many ways.

In chemical pulping, a majority of the lignin is removed from wood pulp (e.g. Kraft process). In the bleaching process chemical pulp is then routinely reacted with chlorine and other delignifying chemicals to further remove lignin and then reacted with bleaching agents to modify the lignin from pulp, whereby providing a stably brightened pulp. However, the treatment with chlorine is undesirable from an environmental standpoint because the resulting effluents contain a large number of toxic compounds (e.g. chlorinated phenolics). Thus alternative bleaching processes are sought by the industry some of which require considerable capital investment or increased amount of chemicals (e.g. chlorine dioxide).

Attempts to use fungi (e.g. white-rot fungi) and enzyme systems from fungi and also bacteria to modify or decrease the lignin in wood pulps to obtain the desired brightening or similar practical effects are disclosed in the literature. However, very few enzyme systems have been found which selectively act on pulp in terms of not adversely affecting the cellulosic content of pulp. Especially xylanase preparations with sufficiently low cellulase activity have been used to delignify wood pulp. Xylanases are enzymes which selectively hydrolyze xylan. To achieve this low cellulase activity the xylanases have to be either separated from cellulases by e.g. ultra-filtration or chromatographic methods or they have to be produced from specially selected microorganisms cultivated under specially optimized conditions. All these enzyme preparations described are only active at a pH in the acidic range and have temperature optima of up to 50° C.

For industrial use, however, it would be a significant advantage if enzymes were available which are active over a wide pH-range, especially pH 7-9 and at a higher temperature.

Xylanases from a *Thermomonospora fusca* strain with the designation MT816 have recently been described (Appl. Microbiol. Biotechnol. (1985) 21:238–244). But no reference has been made to their possible application in pulp delignification.

It has been found, in accordance with this invention, that the enzyme systems of Thermomonospora strains comprising at least one hemicellulase acting enzyme can be used to selectively treat a variety of pulps at a high temperature and under alkaline conditions, whereby the lignin content is reduced while the cellulosic content of the pulp remains substantially unaffected. The preferred enzyme system comprises xylanase. A further preferred enzyme system also contains mannanase and other enzymatic components of *T. fusca* KW3, particularly when softwood pulps are to be treated.

Xylanase is an enzyme which catalyzes the hydrolysis of xylan, a major component of both hardwood and softwood hemicellulose, while mannanase catalyses the hydrolysis of mannan-containing carbohydrates, a major component of softwood hemicellulose.

The enzymes of *T. fusca*, especially the ones of the new strain KW3, act on the hemicellulose/cellulose matrix with which the lignin is associated or bound, such that after treatment of pulp with these enzymes, the lignin is released and/or rendered releasable and can be separated by an appropriate extractant and removed from pulp.

The total enzyme system produced by *T. fusca* KW3 also includes cellulase. It has been found, however, that the supernatants of *T. fusca* KW3, when produced under appropriate conditions, contain only small amounts of cellulase activities which do not adversely affect cellulose and the quality of the paper made therefrom.

While any *T. fusca* may be used in accordance with this invention, the preferred strains include those which produce large quantities of delignifying enzymes which are active at high temperature and under alkaline conditions and can be characterized as enzyme overproducers. An example of such a strain is *T. fusca* KW3 which is deposited in Deutsche Sammlung von Mikroorganismen und Zellkulturen GmbH under No. DSM 6013. The address of the depository is Mascheroder weg 1B, D-3300 Brau Ashweig, Germany and the deposit was made on Jun. 18, 1990. Classification of the new strain as *Thermomonospora fusca* was made by comparing its morphological properties with those of several reference strains using light and electron microscopy. In addition, the new strain had the following biochemical properties typical for *Thermomonospora fusca*: meso-diamino pimelic acid in cell wall, sensitivity towards higher salt concentrations, growth at pH 11 and at 50° C.

The new strain KW3 differs from other known strains, e.g. 'type strain' DSM 43792=ATCC 27730, by its ability to grow at temperatures up to 60° C. and the higher thermostability of its xylanases. KW3 also differs from the strain *T. fusca* MT 816 (Appl. Microbiol. Biotechnol. (1985) 21:238–244) by the higher thermostability of its xylanases, higher xylanase production under the same cultivation conditions and the broader pH-range of the xylanase activity. In addition, the new strain KW3 shows a resistance towards crystal violet which is considered atypical for *Thermomonospora fusca*.

The supernatant is preferably obtained from *T. fusca* cultures which are grown in the presence of a carbon source. The preferred carbon sources include wheat bran, xylan, xylose, mannan (galactomannan, glucomannan or galactoglucomannan), mannose, mechanical pulps, chemical pulps, sawdust, wheat straw, or other substances which contain hemicellulose or are derived from hemicellulose. The micro-organism is cultured on the desired carbon source and optimum enzyme production is typically achieved after 1–5 days. The carbon source has been found to affect the xylanase isoenzyme pattern, i.e. molecular weight, specific activity and pH-optima of individual proteins.

The process of the invention may be carried out in vitro for a time sufficient to decrease the lignin content of the pulp. The process comprises contacting the pulp with a lignin releasing effective amount of an enzyme system comprising lignin releasing enzymes, preferably endo-xylanase, which are contained in the supernatant of a *T. fusca* culture. While the supernatant may be used as such, it is preferably concentrated prior to its use. One highly convenient method of concentration involves a simple ultrafiltration designed to concentrate the supernatant 5-25 fold and in any case recover for use a concentrate containing essentially all enzymes which affect basic wood components, e.g. cellulases, hemicellulases and any enzymes affecting lignin (herein "ligninolytic enzymes"). For this purpose, one may remove all substances which have a molecular weight of less than about 10,000. The resulting concentrate which contains not only the xylanase content of *T. fusca*, but also the cellulase content and other enzymatic activities thereof is effective in decreasing the lignin content of pulp in a selective manner, i.e. without substantially damaging the fiber content desired for paper making.

It is preferred that the process be carried out at a temperature which will enhance the enzymatic activity in vitro. Temperatures may range from approximately 10°-90° C., with 50°-80° being preferred. An even more preferred range is 60°-70°. The preferred pH for the process is 5-10, a more preferred range is 6.5-9.5. It is characteristic for the enzyme preparation of the invention that it is active over a wide pH-range as well as having high activity at pH 7-9 which is the pH of the pulp in the storage towers used by the pulp mills.

The treatment time will vary depending upon factors such as the result desired, the amount of substrate used, the amount of supernatant enzymes used, the specific activity of the supernatant, the type of pulp used, the temperature and the like.

A suitable enzyme dosing is about 0.01 to 200 units/g of dry pulp more preferably 0.1 to 50 units/g. The xylanase activity of the enzyme preparations is determined as follows: To 0.5 ml of xylan solution (1%, Sigma No. X-0627, prepared in 50 mM phosphate buffer, pH 7), 0.5 ml of suitably diluted enzyme in the same buffer is added. The solution is incubated at 70° C. for exactly 10 minutes. The reaction is then stopped by adding 1 ml DNS reagent (3,5-dinitrosalicylate 10 g/l; Na,K tartrate 300 g/l; NaOH 16 g/l), and the color is developed by boiling the sample for 5 minutes. The absorbency is then measured at a wave length of 540 nm. One enzyme unit liberates one micromole of reducing sugars calculated as xylose per minute under assay conditions. The activity is calculated from an enzyme dilution liberating 4 micromoles of reducing sugar under assay conditions.

The present invention may be applied to upgrade or assist in the upgrading of any of a wide variety of processed pulps, i.e. pulps which have been already previously treated in any of a variety of ways to reduce their lignin content and are treated in the process according to the invention to further reduce the lignin content or to enhance the lignin removal by chemical methods or to enhance the drainability of pulps. The invention may be applied to treat mechanical pulps to enhance brightness properties by removing additional lignin therefrom. The invention is particularly applicable to chemical pulps, i.e. those in which the lignin component has been chemically modified by various chemical treatments such as in the sulfite, organosolv, soda and the sulfate (Kraft) processes and oxygen bleaching, and is preferably applied to Kraft pulps.

The particularly applicable pulps will generally already have 80 to 99% of their lignin removed and are treated essentially to remove additional lignin including chemically modified lignin. Such treatment of chemical pulps is commonly referred to as bleaching and may be evidenced by a brightening of the pulp.

The resulting pulp is treated to remove the releasable lignin component using an appropriate extractant. Such extractants essentially solubilise the affected lignin component and suitable extractants include but are not limited to bases such as alkali metal hydroxides (E), DMF, dioxane, acetone, and alcohol. Hydroxide extractions may be combined with hydrogen peroxide ($E_p$) or oxygen ($E_o$). The resulting pulp may then be further bleached by a chemical bleaching sequence to the desired brightness whereby substantial savings of chemicals are observed when compared to pulp bleached to the same brightness by the same sequence but without using the enzyme treatment. Elemental chlorine free bleaching can be achieved in such a way.

The removal of small amounts of hemicellulose and amorphous cellulose in addition to the decrease of the lignin content of any pulp when treated with the describe enzyme preparation gives rise to additional benefits such as increased drainability and decreased water retention of the pulp.

The present invention may be illustrated by reference to the following Examples.

EXAMPLES

Example 1

Cultivation of *Thermomonospora fusca* KW3

A. Culture Medium for Shaker Flask Cultures

*T. fusca* strain KW3 is grown and stored on plates with LB medium or in liquid LB medium. LB medium contains:

| LB Medium | |
|---|---|
| peptone | 15 g |
| yeast extract | 5 g |
| sodium chloride | 5 g |
| glucose.$H_2O$ | 1.1 g |
| agar | 20 g (for plates only) |
| distilled water | fill up to 1000 ml |
| adjusted to pH 7.5 before autoclaving | |

The cultivation for enzyme production is carried out in the following medium:

| Medium for Shaker Flasks | |
|---|---|
| M6 | 100 ml |
| yeast extract | 1 g |
| trace element solution | 1 ml |
| substrate | 2-20 g |
| distilled water | fill up to 1000 ml |
| adjusted to pH 7.2 before autoclaving | |

To stabilize the pH during cultivation 12.5 ml phosphate buffer (0.1M, pH 8.0) was added to 250 ml of this medium.

| Mineral Salt Medium M6 | |
|---|---|
| $(NH_4)_2SO_4$ | 3 g |
| NaCl | 3 g |

| -continued | |
|---|---|
| MgSO$_4$ | 1 g |
| CaCO$_3$ | 0.2 g |
| distilled water | fill up to 1000 ml |
| Trace Element Solution | |
| ZnCl$_2$ | 40 mg |
| FeCl$_3$ | 200 mg |
| CuCl$_2$.2H$_2$O | 10 mg |
| MnCl$_2$.4H$_2$O | 10 mg |
| Na$_2$B$_4$O$_7$.10H$_2$O | 10 mg |
| (NH$_4$)$_2$Mo$_7$O$_{24}$.4H$_2$O | 10 mg |
| distilled water | fill up to 1000 ml |

Substrates

1% xylan from oat spelts (practical grade, Sigma) or 1% galactomannan (Sigma) or 0.5% commercial wheat bran was added before autoclaving.

Inoculum Preparation

Either spores or mycelium from an agar slant or a frozen test tube culture were added to 100 ml of LB medium. This shaker flask was placed on a shaker for 48 hrs, at 48° C. and 150 rpm. From this culture 10% of the final cultivation volume was used as an inoculum.

Cultivation

The cultivation was carried out in 1 liter shaker flasks with 250 ml culture medium each at 48° C. and 150 rpm. Maximum xylanase or mannanase activity was detected after 2–3 days. The culture supernatant was harvested by centrifugation (3000 rpm, 10 min.) and filtration through a cellulose filter. Xylanase activities of around 5 Ul$^{-1}$ and mannanase activities of around 1 Ul$^{-1}$ were obtained for cultures grown on oat spelt xylan and 3 Ul$^{-1}$ and 0.5 Ul$^{-1}$ respectively for cultures grown on wheat bran.

B. Enzyme Production in a 15 Liter Bioreactor

Bioreactor equipment

A 15 liter bioreactor, with a working volume of 10 liter (MBR, Sulzer; Switzerland) was used.

Inoculum Preparation

Growing cultures were started by inoculating 1000 ml shaker flasks, containing 250 ml LB medium, with a frozen test tube culture. Flasks were placed on a shaker for 48–55 hrs, at 48° C. and 150 rpm. 500 ml were used to inoculate the bioreactor.

| Composition of the bioreactor medium MorM3 | |
|---|---|
| xylan | 3 gl$^{-1}$ |
| yeast extract | 1 |
| NaCl | 1.5 |
| (NH$_4$)$_2$SO$_4$ | 3.1 |
| KH$_2$PO$_4$ | 0.2 |
| salt solution | 10 mll$^{-1}$ |
| vitamin solution | 1 mll$^{-1}$ |
| pH adjusted to 7.2 with NAOH | |
| Vitamin Solution | |
| Thiamin.HCl | 1 mgl$^{-1}$ |
| Biotin | 1 mgl$^{-1}$ |
| Salt Solution | |
| Na$_3$EDTA | 5 gl$^{-1}$ |
| MgSO$_4$.7H$_2$O | 20 |
| ZnSO$_4$.7H$_2$O | 0.8 |
| MnSO$_4$.H$_2$O | 1.5 |
| FeSO$_4$.7H$_2$O | 2 |
| CaCl$_2$ | 2 |

Cultivation

The cultivation was carried out at 48° C., 500 rpm (normal blade stirrer). The fermentation broth was aerated at 0.5 (v/v/min) and the pH was kept automatically at 7.2 (NaOH 2N) The maximum xylanase activity was detected after 1–2 days. The culture supernatant was harvested by centrifugation (5000 rpm, 10–60 min.). Xylanase activity was usually around 40,000 Ul$^{-1}$ and the CMCase activity less than 1%.

The production of mannanase was carried out according to the same procedure except that galactomannan was used instead of xylan.

Example 2

Analysis of Enzyme Supernatant

Culture supernatants from shake flask cultures, obtained as described in Example 1, showed the following enzymatic activities ($\mu$Mols of reducing sugar/min./ml):

| | Enzyme activities ($\mu$mol/min/ml) | | |
|---|---|---|---|
| C-SOURCE | XYLANASE | MANNANASE | CELLULASE (CMC) |
| wheat bran | 2.1 | 0.06 | 0.08 |
| xylan | 5.3 | 0.2 | 0.02 |
| galactomannan | 2.6 | 1.6 | 0.08 |

Assays to determine the enzyme activities were carried out as follows:

Xylanase Activity

To 0.5 ml of xylan suspension (1%, Sigma No. X-0627, prepared in 50 mM phosphate buffer, pH 7) 0.5 ml of suitably diluted enzyme (to give OD$_{540}$ from 0.1 to 0.9) in the same buffer was added. The solution was incubated at 70° C. for exactly 10 minutes. The reaction was then stopped by adding 1 ml DNS reagent (3,5-dinitrosalicylate 10 g/l; Na-K-tartrate 300 g/l; NaOH 16 g/l), and the colour was developed by boiling the samples for 5 minutes. After adding 5 ml of H$_2$O the absorption was measured at 540 nm. One enzyme unit liberates one micromole of reducing sugar calculated as xylose per min under assay conditions.

Mannanase Activity

The same procedure as that for endo-xylanase was used except that galactomannan (Sigma No. G-0753) was used instead of xylan.

Cellulase Activity

The determination was carried out according to the procedure recommended by the International Union of Pure and Applied Chemistry (IUPAC) using carboxymethyl cellulose (CMC, Fluka No. 21901) as a substrate (Pure & Applied Chemistry, Vol. 59 (2), 257-268 (1987)) with the following modifications: phosphate buffer pH 7, 70° C.

Analysis of the culture supernatant by SDS polyacrylamide gel electrophoresis reveals a set of at least 6 isoenzymes with xylanase activity. The main band shows a relative molecular weight of ca. 20,000. Analysis by isoelectric focusing, polyacrylamide gel electrophoresis and subsequent activity staining reveals 6 bands with xylanase activity of which the main component had an isoelectric point of 4.5 and an M$_r$ of 20 kDalton. The same procedure showed 4 mannanase isoenzymes.

Further analysis of the respective crude supernatants showed that the preparations retained more than 50% of their maximal activities in the pH range from 5.5 to 9, with a maximal activity at pH 6–7 measured at 70° C. The optimal temperature at pH 7 is 60°–70° C. but at 80° C. still more than 30% of the maximal activities remain.

| Activity (% of maximum) | | | |
|---|---|---|---|
| pH | xylanase | mannanase | CMCase |
| pH profile of enzyme activities at 70° C. | | | |
| 4.5 | 8 | — | 92 |
| 5.0 | 50 | 87 | 100 |
| 5.5 | 70 | — | 95 |
| 6.0 | 85 | — | 96 |
| 6.5 | 100 | 100 | 93 |
| 7.0 | 100 | 96 | 84 |
| 7.5 | 82 | — | 80 |
| 8.0 | 62 | 93 | 78 |
| 8.5 | 60 | — | 71 |
| 9.0 | 50 | 73 | 66 |
| 9.5 | 35 | — | 64 |
| Temperature profile of enzyme activities at pH 7 | | | |
| Temp. °C. | | | |
| 20 | — | — | 48 |
| 30 | 16 | — | 56 |
| 40 | — | 57 | 76 |
| 50 | 60 | 67 | 81 |
| 60 | 96 | 86 | 88 |
| 70 | 100 | 100 | 100 |
| 80 | 58 | 30 | 35 |
| 90 | 11 | — | 15 |

The stability of the xylanase activity in the crude supernatant was checked at pH 7 and 9. Results are as follows.

| | relative activity (%) | | |
|---|---|---|---|
| Hours | 25° C. | 60° C. | 70° C. |
| Xylanase stability at pH 7 | | | |
| 0 | 100 | 100 | 100 |
| 1 | — | — | 95 |
| 2 | — | — | 90 |
| 7 | 100 | 100 | 66 |
| 23 | 100 | 95 | 8 |
| 32 | 100 | — | 2 |
| 49 | 96 | 90 | 0 |
| 97 | — | 76 | — |
| Xylanase stability at pH 9 | | | |
| 0 | 100 | 100 | 100 |
| 1 | — | — | . |
| 2 | — | — | — |
| 7 | 100 | — | 44 |
| 23 | 100 | 55 | 8 |
| 32 | 100 | — | 2 |
| 49 | 100 | — | 0 |
| 97 | 96 | 20 | — |

Example 3

Delignification of Kraft Pulp

Enzyme Preparation

The crude enzyme preparation obtained as described in example 1 was concentrated by use of an ultrafiltration membrane (molecular weight cut off 10,000) to a concentration of 2500 xylanase units per milliliter.

Alternatively the crude enzyme preparation was lyophilised. The dry powder was then dissolved in a volume 10 times smaller than the original volume and dialyzed (molecular weight cut off 10,000) against the 100-fold volume of phosphate buffer pH 7.

Pulp Treatment

Hardwood and softwood Kraft pulp (2.5 % consistency) was incubated with the indicated amount of enzyme indicated as number of xylanase units for 2 hours at 70° C. Prior to the addition of enzyme the pH was adjusted to 7 by addition of hydrochloric acid and to 9 by addition of sodium hydroxide. The enzyme dose indicated was the activity measured under standard conditions (Example 2). After 2 hours time the pulp suspension was filtered through a Whatman No. 1 filter paper. The pulp was further extracted under alkaline conditions (2.5% NaOH/g of pulp, 1 hour at 50° C.) and air dried. The delignification was measured as change in Kappa number. The extent of delignification and bleachability of the pulp may be indicated by the Kappa number. A lower Kappa number is desirable as it indicates that a smaller amount of lignin is present.

Determination of Kappa Number

The Kappa number is the volume (in milliliters) of 0.1N potassium permanganate solution consumed by one gram of moisture-free pulp under the conditions specified in this method. The results are corrected to 50% consumption of the permanganate added. The following standard method was used: TAPPI Test methods, (Tappi, Atlanta, Ga.), Vol. 1, 1988 "Kappa number of pulp—T 236 cm 85".

| | pH 7 | | pH 9 | |
|---|---|---|---|---|
| Enzyme dose (U/g pulp) | Kappa No. | viscosity (%) | Kappa No. | viscosity (%) |
| Delignification of hardwood Kraft pulp | | | | |
| 0 | 14.6 | 100 | 14.8 | 100 |
| 1 | 14.6 | | 14.7 | |
| 5 | 14.1 | | 14.0 | |
| 10 | 13.9 | | 13.9 | |
| 50 | 13.4 | 105 | 13.2 | 102 |
| Delignification of softwood Kraft pulp | | | | |
| 0 | 19.1 | 100 | 19.0 | 100 |
| 10 | 18.7 | 100 | 18.6 | 99 |
| 50 | 18.1 | — | 18.0 | — |

Example 4

Elemental Chlorine Free Bleaching of Hardwood Kraft Pulp

Eucalyptus Kraft pulp with a Kappa number of 18.5 was treated with 20 U/g pulp of xylanase activity for 3 hours at 80° C., pH 9 and a pulp consistency of 15%. The resulting pulp was further bleached chemically using the following sequence under standard conditions: $E_PD_1 E_PD_2$. To illustrate the advantage obtained by using the enzyme two common bleaching sequences were also applied.

| | Pulp properties | | | |
|---|---|---|---|---|
| Sequence | yield (%) | viscosity (dm³/kg) | brightness (% ISO) | active chlorine (kg/t) |
| unbleached | — | 1350 | 35.5 | — |
| $(D_{50}C_{50})E_PD_1E_PD_2$ | 93.9 | 1150 | 88.8 | 53.2 |
| $CE_PD_1E_PD_2$ | 93.5 | 1160 | 88.9 | 58.8 |
| $-E_PD_1E_PD_2$ | 95.4 | 1230 | 85.0 | 50.0 |
| $EnzE_PD_1E_{PD2}$ | 92.8 | 1170 | 88.8 | 49.6 |

The data show that, by using the enzyme, considerably less active chlorine is needed to reach the same brightness level than with common bleaching sequences.

Similar results were obtained at pH 7. Paper property tests at °SR of 20, 40 and 60 respectively revealed no significant differences between enzyme and chlorine containing sequences.

Example 5

Elemental Chlorine Free Bleaching of Softwood Kraft Pulp

Oxygen bleached spruce Kraft pulp with a Kappa number of 17.9 was treated with 3 U/g pulp of xylanase activity for 5 hours at 70° C. pH 7 and a pulp consistency of 15%. The resulting pulp was further bleached using the following sequence under standard conditions: $D_1E_{OP}D_2E_PD_3$ ($D_1$ run like a C-stage).

|  | Pulp properties | | | |
|---|---|---|---|---|
| Sequence | yield (%) | viscosity ($dm^3$/kg) | brightness (% ISO) | active chlorine (kg/t) |
| unbleached | — | 1050 | 35.5 | — |
| —$D_1E_{OP}D_2E_PD_3$ | 95.0 | 980 | 87.9 | 61.0 |
| Enz$D_1E_{OP}D_2E_PD_3$ | 95.0 | 1000 | 88.4 | 48.0 |

The data show again that, by using the enzyme, considerably less active chlorine is needed to reach the same brightness level than with a no elemental chlorine containing bleaching sequence. The paper properties, compared at the same °SR, remained unchanged.

We claim:

1. A process for the bleaching of pulp which comprises the step of: contacting the pulp with a lignin releasing effective amount of an enzyme system of the fungus *Thermomonospora fusca* which system exhibits xylanase activity so to release lignin from the pulp without substantially affecting the cellulosic content of the pulp at a temperature of at least 50° C. and at a pH suitable for releasing lignin.

2. The process according to claim 1 wherein the strain of *Thermomonospora fusca* is a strain with the designation KW3 and a deposition number of DSM 6013.

3. The process according to claim 1 wherein the process includes the preceding steps of:
   growing the *Thermomonospora fusca* strain under conditions appropriate for producing a xylanase;
   centrifuging the culture resulting from the growth of the *Thermomonospora fusca* to obtain a supernatant containing at least a xylanase obtained from the *Thermomonospora fusca*; and subsequently contacting the pulp with the supernatant containing the at least a xylanase obtained from the *Thermomonospora fusca*.

4. The process according to claim 1 wherein the pulp is at a temperature of at least 50° C. and at a pH in the range of 5–10.

5. The process according to claim 1 wherein the pulp is contacted at a temperature of at least 50° C. with the enzyme system at an enzyme dosing ratio in the range of about 0.01–200 units of xylanase activity per gram of dry pulp.

6. The process according to claim 5 wherein the pulp is contacted at a temperature of at least 50° C. with the enzyme system at an enzyme dosing ratio in the range of about 0.1–50 units of xylanase activity per gram of dry pulp.

7. The process according to claim 1 wherein the pulp is selected from the group consisting of: kraft pulp, hardwood pulp or softwood pulp.

8. A process according to claim 1 wherein the pulp is chemical pulp.

9. A process according to claim 1 wherein the enzyme system further comprises a mannanase.

10. A process according to claim 1 which comprises the further process step of: extracting the contacted pulp to remove lignin released by the enzyme system.

11. A process for the bleaching of a kraft pulp, a hardwood pulp or a softwood pulp in order to reduce the lignin content thereof which process includes the steps of:
   growing a *Thermomonospora fusca* strain in a culture medium and under conditions appropriate for producing a xylanase wherein the strain of *Thermomonospora fusca* is a strain with the designation KW3 and a deposition number of DSM 6013;
   centrifuging the culture resulting from the growth of the *Thermomonospora fusca* to obtain a supernatant which contains at least a xylanase obtained from the *Thermomonospora fusca*; and,
   contacting the pulp at a temperature of at least 50° C. and at a pH suitable for releasing lignin with the supernatant of the strain of *Thermomonospora fusca* in order to release lignin from the pulp.

12. The process according to claim 1 wherein the pulp is contacted at an enzyme dosing ratio in the range of about 0.01–200 units of xylanase activity per gram of dry pulp.

* * * * *